United States Patent
Imai

(10) Patent No.: US 6,995,576 B2
(45) Date of Patent: Feb. 7, 2006

(54) THIN FILM TRANSISTOR ARRAY INSPECTION APPARATUS

(75) Inventor: Daisuke Imai, Hadano (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/990,415

(22) Filed: Nov. 18, 2004

(65) Prior Publication Data

US 2005/0139771 A1    Jun. 30, 2005

(30) Foreign Application Priority Data

Dec. 24, 2003  (JP) .............................. 2003-426759

(51) Int. Cl.
*G01R 31/305*  (2006.01)

(52) U.S. Cl. ...................... 324/751; 324/770

(58) Field of Classification Search .................... None
See application file for complete search history.

(56) References Cited

U.S. PATENT DOCUMENTS

| | | | | |
|---|---|---|---|---|
| 4,730,158 A * | 3/1988 | Kasai et al. | ................. | 324/751 |
| 6,657,192 B1 * | 12/2003 | Kim et al. | ................... | 250/310 |
| 6,703,850 B2 * | 3/2004 | Nozoe et al. | ................ | 324/751 |
| 6,734,687 B1 * | 5/2004 | Ishitani et al. | ................ | 324/751 |
| 6,753,524 B2 * | 6/2004 | Matsui et al. | ................ | 250/310 |
| 2002/0093350 A1 * | 7/2002 | Yamada | ....................... | 324/751 |
| 2004/0017212 A1 * | 1/2004 | Litman et al. | ............... | 324/751 |

\* cited by examiner

*Primary Examiner*—Vinh Nguyen
*Assistant Examiner*—Richard Isla-Rodas
(74) *Attorney, Agent, or Firm*—Manabu Kanesaka

(57) ABSTRACT

A TFT array inspection apparatus includes an electron beam source for irradiating an electron beam, a detecting device for detecting an electron beam emitted from a sample upon irradiating the electron beam to output a detected signal, and a sample potential changing device for changing a sample potential. A calibration device calibrates the detected signal using a calibration curve of the sample potential and the detected signal to obtain the sample potential.

7 Claims, 7 Drawing Sheets

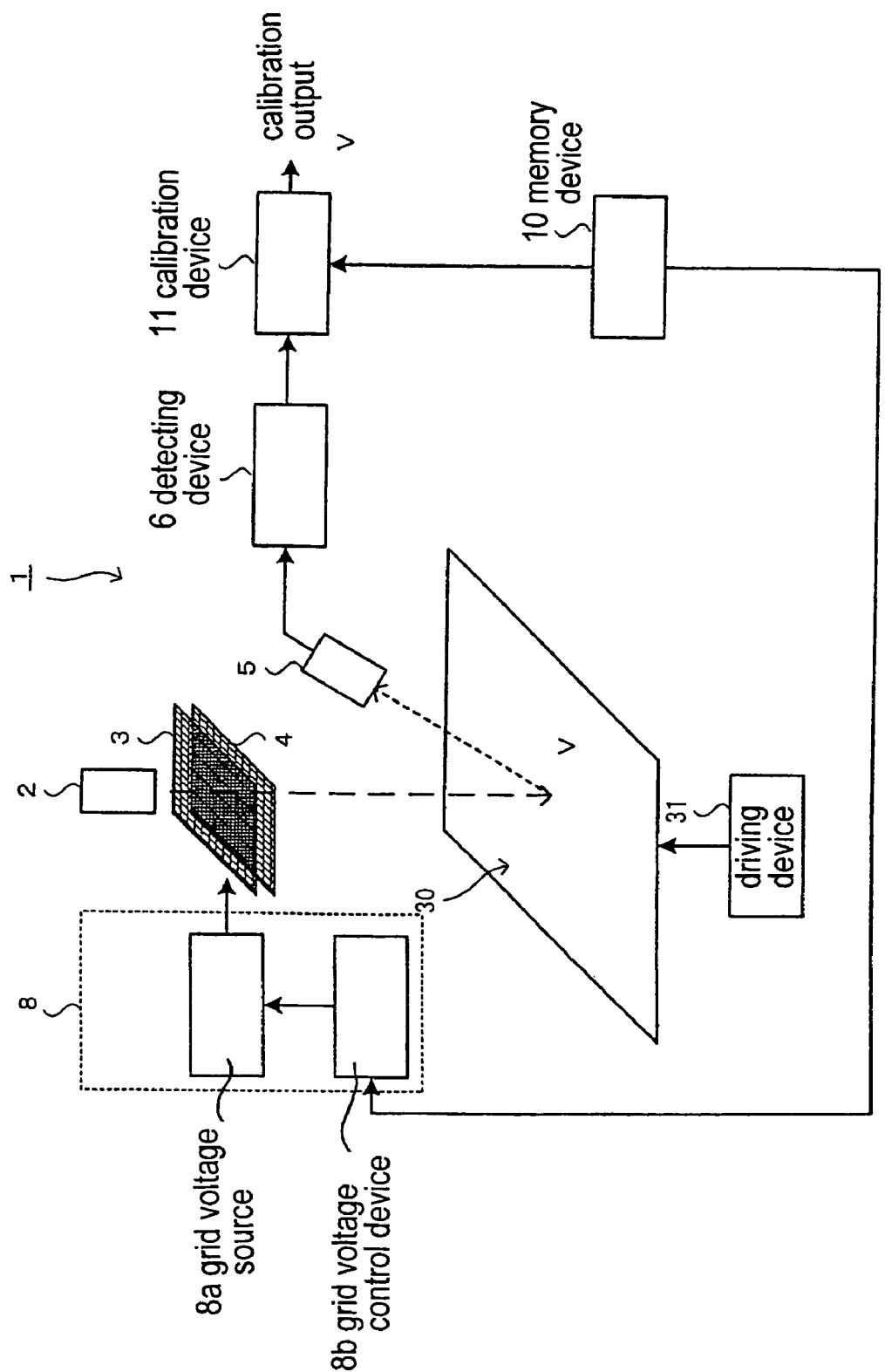

THIN FILM TRANSISTOR ARRAY INSPECTION APPARATUS

BACKGROUND OF THE INVENTION AND RELATED ART STATEMENT

The present invention relates to a thin film transistor (TFT) array inspection apparatus for inspecting a TFT array base plate used for a liquid crystal display, organic electroluminescence (EL) display and the like. More specifically, the present invention relates to an apparatus for inspecting a TFT array by measuring a potential state through a secondary electron obtained by irradiating an electron beam.

A scanning beam apparatus scans a charge beam such as an electron beam and ion-beam on a sample two-dimensionally for forming a scan image. Such a scanning beam apparatus includes an electron beam micro-analyzer, scanning electron microscope, X-ray diffractometer, TFT array inspection apparatus, or the like. Such a scanning beam apparatus described above also includes a defect inspection apparatus for inspecting a defect of picture elements by irradiating an electron beam to a liquid panel matrix base plate and measuring signal strength of a secondary electron beam or the like emitted from the base plate (for example, refer to Patent Document 1).

In order to inspect a base plate state for detecting a picture element defect or the like based on the signal strength of the secondary electron beam, it is necessary to calibrate the signal strength. If the signal strength is not calibrated, it is difficult to accurately inspect the base plate state and compare different base plates.

Conventionally, the scanning beam apparatus does not include a device for calibrating the detected signal strength. Instead, the signal strength is obtained with respect to a standard sample, and a comparison is made based on the standard strength.

On the other hand, in the apparatus using the electron beam, an electron gun as a source of the electron beam is calibrated. In a method of calibrating the electron gun, for example, there are a known method in which a grid disposed at a sample position is scanned and observed to obtain a grid image; and a method in which a filament current flowing through a filament of the electron gun, an emission current of an current source of the electron gun, a beam current irradiated from the electron gun, or the like, is measured.

FIG. 7 is a view for explaining the calibration of a conventional electron gun. In FIG. 7, in a scanning beam apparatus 21, an electron gun 22 irradiates an electron beam to a sample 30. A secondary beam or the like emitted from the sample 30 is detected by a detector 25, and a detecting device 26 obtains a detected signal. The calibration of the electron gun 22 is carried out by observing a grid image of a grid 23 disposed on the sample 30 or by measuring a filament current and emission current obtained from the electron gun 22, or an irradiated beam current.

Patent Document 2 has disclosed a calibration method by measuring an emission current, and Patent Document 3 has disclosed a calibration method by measuring a beam current.

Patent Document 1: Japanese Patent Publication (Kokai) No. 01-292736

Patent Document 2: Japanese Patent Publication (Kokai) No. 2001-150468

Patent Document 3: Japanese Patent Publication (Kokai) No. 2003-36807

In the conventional method of calibrating the electron gun, only the grid image is observed, or only the electric current relating to the electron gun is measured, and a relationship with respect to an object to be measured is not obtained. Accordingly, when the conventional method of calibrating the electron gun is applied to the scanning beam apparatus, while the electron gun can be calibrated, the detected signal strength is not calibrated.

Especially, the TFT array inspection apparatus inspects a defect in a base plate of a TFT array based on the potential strength on the base plate. Accordingly, even if the conventional technique of calibrating the electron gun is employed, it is difficult to calibrate the detected signal strength to obtain the potential strength on the base plate.

In view of the problems described above, the present invention has been made, and an object of the invention is to provide a TFT array inspection apparatus capable of calibrating detected signal strength to obtain potential strength on a base plate.

Further objects and advantages of the invention will be apparent from the following description of the invention.

SUMMARY OF THE INVENTION

In order to attain the objects described above, according to the present invention, a calibration curve is obtained through detected signal strength with respect to a potential change of a sample, and the detected signal strength is calibrated using the calibration curve to obtain a sample potential.

According to the present invention, a TFT array inspection apparatus includes: an electron beam source for irradiating an electron beam; a detecting device for detecting an electron beam emitted from a sample upon irradiating the electron beam to output a detected signal; a sample potential changing device for changing a sample potential; and a calibration device for calibrating the detected signal using a calibration curve of the sample potential and the detected signal to obtain the sample potential.

The detecting device detects a change of the sample potential by the sample potential changing device as well as the detected signal. Accordingly, it is possible to obtain a signal strength curve of the detected signal with respect to the change of the sample potential. The calibration device obtains the sample potential from the detected signal strength using the signal strength curve as the calibration curve.

According to the present invention, the TFT array inspection apparatus may include a calibration curve forming device for forming the calibration curve. In the calibration curve forming device, the sample potential is inputted from the sample potential changing device, and the detected signal strength is inputted from the detecting device. The calibration curve is formed through the detected signal strength with respect to the potential change of the inputted sample potential.

According to the present invention, in the TFT array inspection apparatus, the calibration device may include a plurality of calibrating curves obtained under different conditions. When the detected signal is calibrated, a calibration curve suitable for measuring the sample potential to be measured is selected from the plural calibration curves, and the detected signal is calibrated using the selected calibration curve. Accordingly, it is possible to select, for example, a calibration curve with good linearity in a range of the sample potential to be measured, so that the sample potential has excellent linearity with respect to the detected signal strength after the calibration.

According to the present invention, the TFT array inspection apparatus may include a calibration curve forming device for forming the calibration curve. The calibration curve forming device receives the sample potential from the sample potential changing device per every different measuring condition, and receives the detected signal strength from the detecting device. The calibration curve forming device forms the calibration curve per every different measuring condition through the detected signal strength with respect to the change of the inputted sample potential.

According to the present invention, a grid may be disposed at a downstream side of the electron beam source, and a grid potential setting device may be provided for applying a voltage to the grid for setting the measuring condition. The measuring condition is set through the grid potential. The sample potential changing device changes the sample potential per every grid potential, and the detecting device detects the detected signal.

In the TFT array inspection apparatus of the invention, it is possible to accurately obtain the potential strength on the base plate through calibrating the detected signal strength.

BRIEF DESCRIPTION OF THE DRAWINGS

FIG. 5 is a schematic diagram for explaining an operation of the TFT array inspection apparatus according to the embodiment of the invention;

DETAILED DESCRIPTION OF PREFERRED EMBODIMENT

Figure 1:
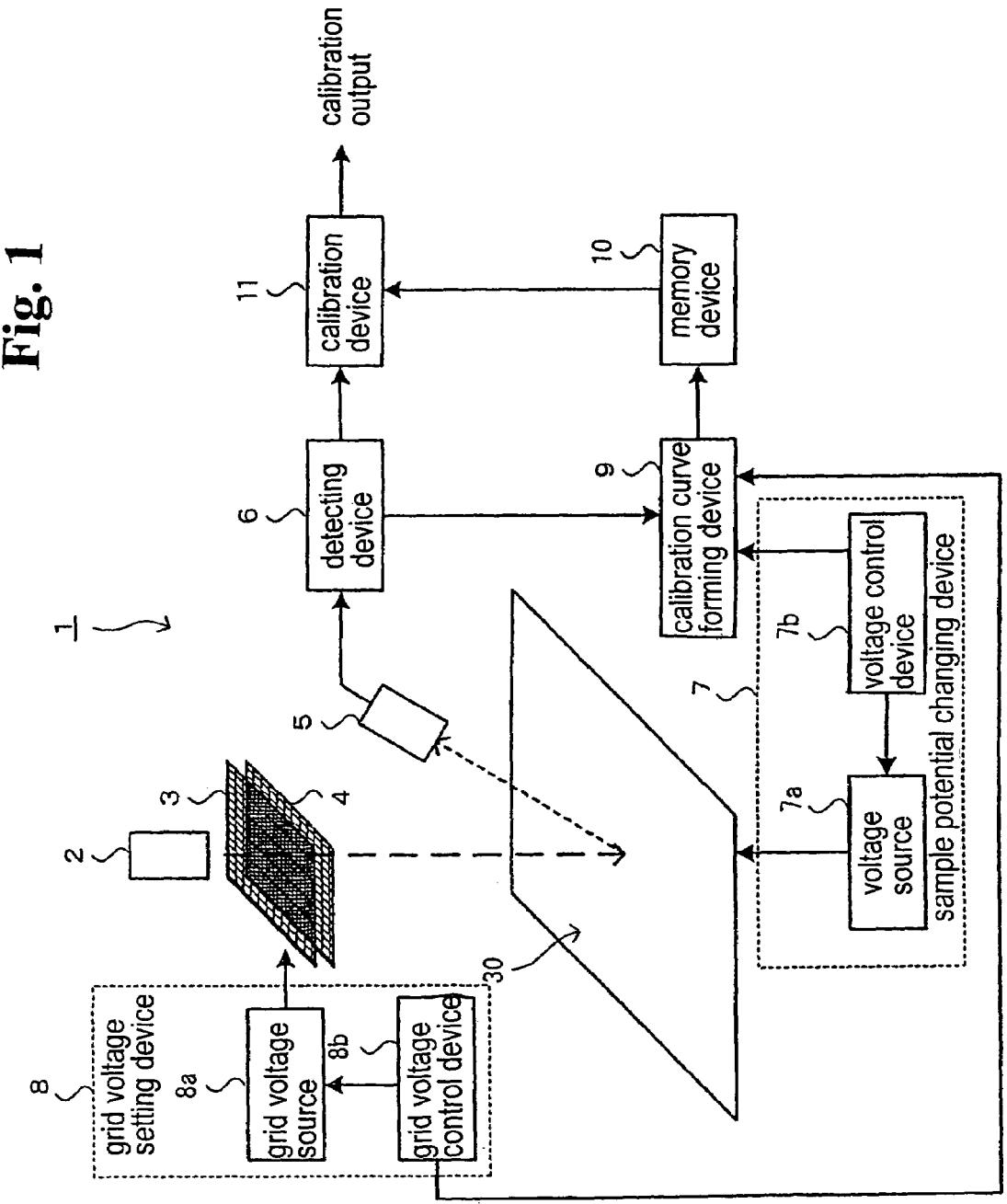
FIG. 1 is a schematic diagram for explaining an outline of a TFT array inspection apparatus according to an embodiment of the invention.

Hereunder, embodiments of the present invention will be explained with reference to the accompanying drawings. FIG. 1 is a schematic view for explaining a TFT array inspecting device according to the embodiment of the invention. As shown in FIG. 1, a TFT array inspection apparatus 1 includes an electron beam source 2 for irradiating an electron beam; a detector 5 for detecting an electron beam such as a secondary electron emitted from a sample 30 of a TFT array and the like upon irradiation of the electron beam; and a detecting device 6 for obtaining a signal strength of the detected signal of the detector 5.

The TFT array inspection apparatus 1 obtains a potential on the TFT array based on the signal strength of the detected signal, and inspects a defect and the like of the TFT array from a potential state thereof. The TFT array inspection apparatus includes, as a structure for calibrating the detected signal strength, grids 3 and 4 disposed at a downstream side of the electron beam source 2; a grid potential setting device 8 for setting a potential to the grids 3 and 4; a sample potential changing device 7 for changing the potential of the sample 30; a calibration curve forming device 9 for forming a calibration curve based on the detected signal and sample potential in advance; a memory device 10 for storing the calibration curve; and a calibration device 11 for calibrating the detected signal strength based on the calibration curve.

The grids 3 and 4 are provided with a filtering function for selectively passing only electrons having specific energy among the electron beams emitted from the electron beam source 2. Accordingly, it is possible to select energy of the electron beam passing therethrough according to the potentials of the respective grids and a potential difference between the grids.

The grid potential setting device 8 includes a grid voltage source 8a and a grid voltage control device 8b for controlling a voltage generated by the grid voltage source 8a. The grid potential setting device 8 controls the voltages applied to the grids 3 and 4 to set the potentials of the grids 3 and 4. The sample potential changing device 7 includes a voltage source 7a for applying a voltage to the sample 30 and a voltage control device 7b for controlling the voltage generated by the voltage source 7, so that the voltage applied to the sample 30 is changed. While the sample potential changing device 7 changes the potential of the sample 30, the detecting device 6 obtains the detected signal strength to determine a characteristic of the signal strength with respect to the sample potential, so that the calibration curve can be formed.

The calibration curve forming device 9 receives the detected signal strength from the detecting device 6 and the potential of the sample 30 from the sample potential changing device 7, so that the characteristic of the signal strength with respect to the sample potential is determined. The characteristic represents a relationship between the sample potential and the detected signal strength. Accordingly, the characteristic can be used as the calibration curve for obtaining the potential of the sample 30 from the signal strength detected by the detector 5 and detecting device 6. The calibration curve formed by the calibration curve forming device 9 is stored in the memory device 10.

The calibration device 11 obtains the potential of the sample 30 from the signal strength detected by the detecting device 6 using the calibration curve stored in the memory device 10. The characteristic of the signal strength with respect to the sample potential depends on energy of the electron beam irradiated to the sample. The TFT inspection apparatus 1 of the invention includes the grid potential setting device 8 for setting the energy of the electron beam irradiated to the sample. Accordingly, it is possible to set a potential measurement range of the sample 30 through the potentials of the grids 3 and 4, and a strength width of the detected signal strength through a potential difference between the grids 3 and 4.

While the grid potential setting device 8 changes the potential of the grids 3 and 4, the calibration curve is formed. Accordingly, it is possible to obtain a plurality of calibration curves with different grid potentials. The calibration device 11 selects a calibration curve suitable for a potential range of the sample 30, and obtains the potential of the sample 30 from the detected signal strength using the selected calibration curve.

Figure 2:
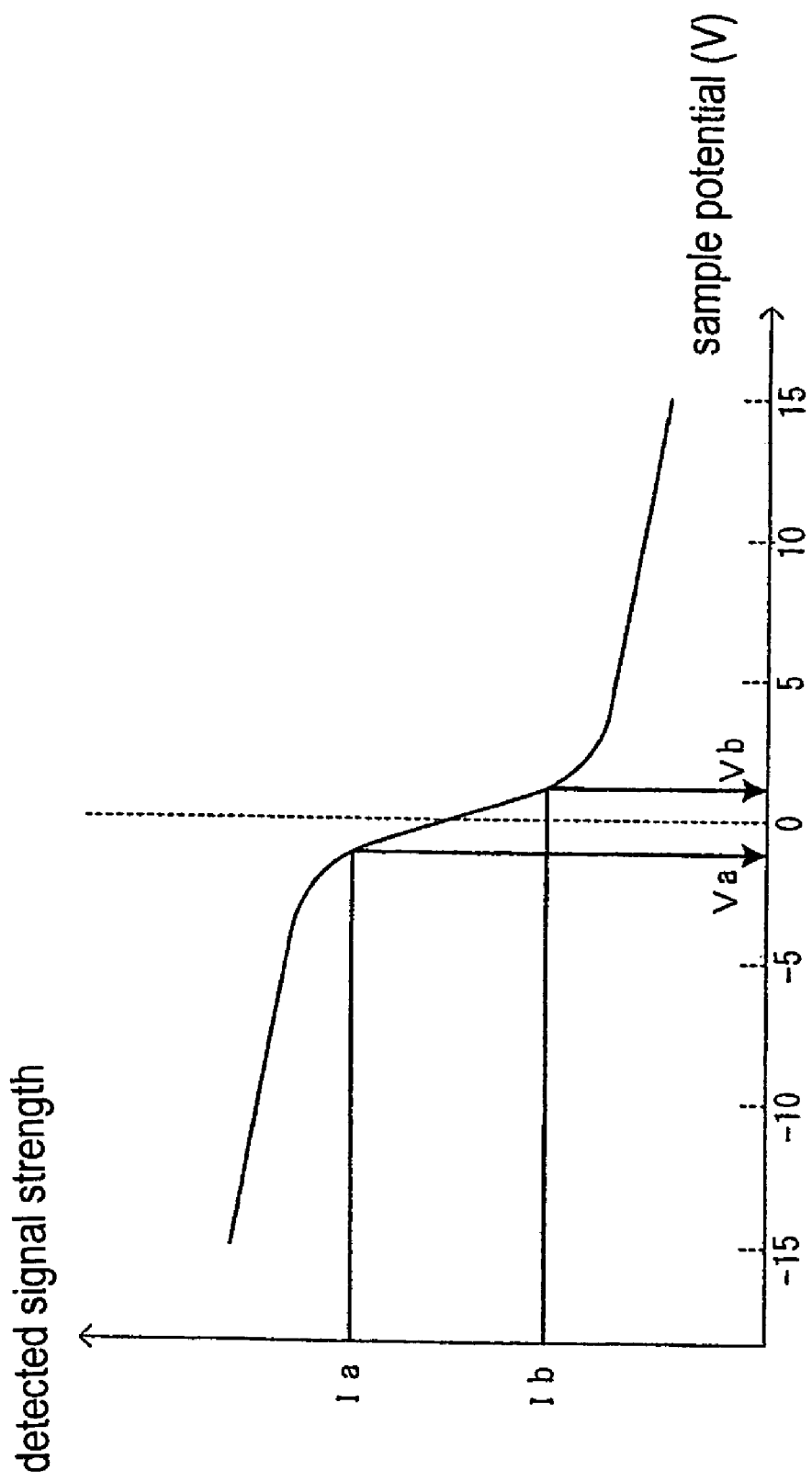
FIG. 2 is a graph showing an example of a calibration curve according to the embodiment of the invention.

FIG. 2 is a graph showing an example of the calibration curve, wherein the abscissa axis represents the sample potential and the ordinate axis represents the detected signal strength. As described above, while the sample potential changing device 7 changes the potential applied to the sample 30, the detected signal strength obtained by the detecting device 6 is plotted to obtain the calibration curve. When the calibration curve is used, a sample potential on the calibration curve is determined with respect to, for example, the detected signal strength Ia to obtain a sample potential Va.

Figure 6A:
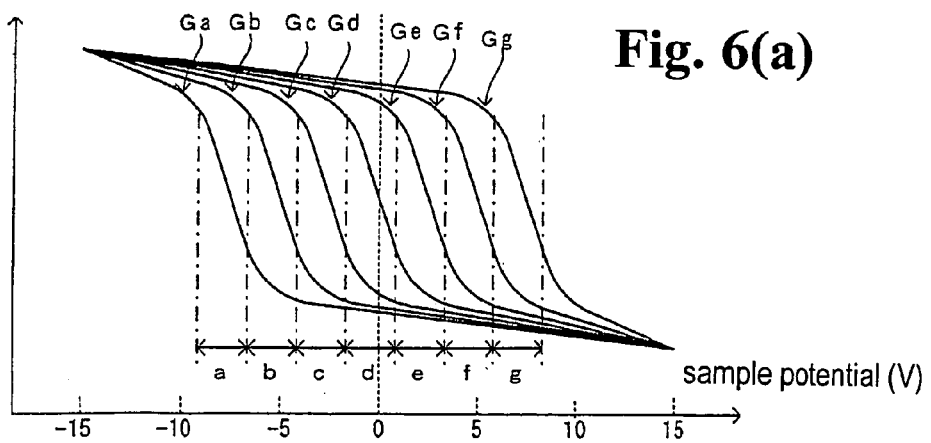
FIGS. 6(a) to 6(c) are explanatory drawings for explaining processes of obtaining calibration outputs from calibration curves according to the embodiment of the invention.

FIG. 6(a) shows a plurality of calibration curves with respect to different grid potentials. That is, FIG. 6(a) shows the calibration curves with respect to the different grid potentials Ga to Gg. Each of the calibration curves includes a portion with good linearity and a portion with poor linearity between the signal strength change and the sample potential change. When the sample potential is measured, it is possible to increase measurement accuracy by using the portion with good linearity between the sample potential and the signal strength. Accordingly, it is possible to perform accurate measurement by selecting a proper calibration curve corresponding to a range of the sample potential to be measured.

Figure 3:
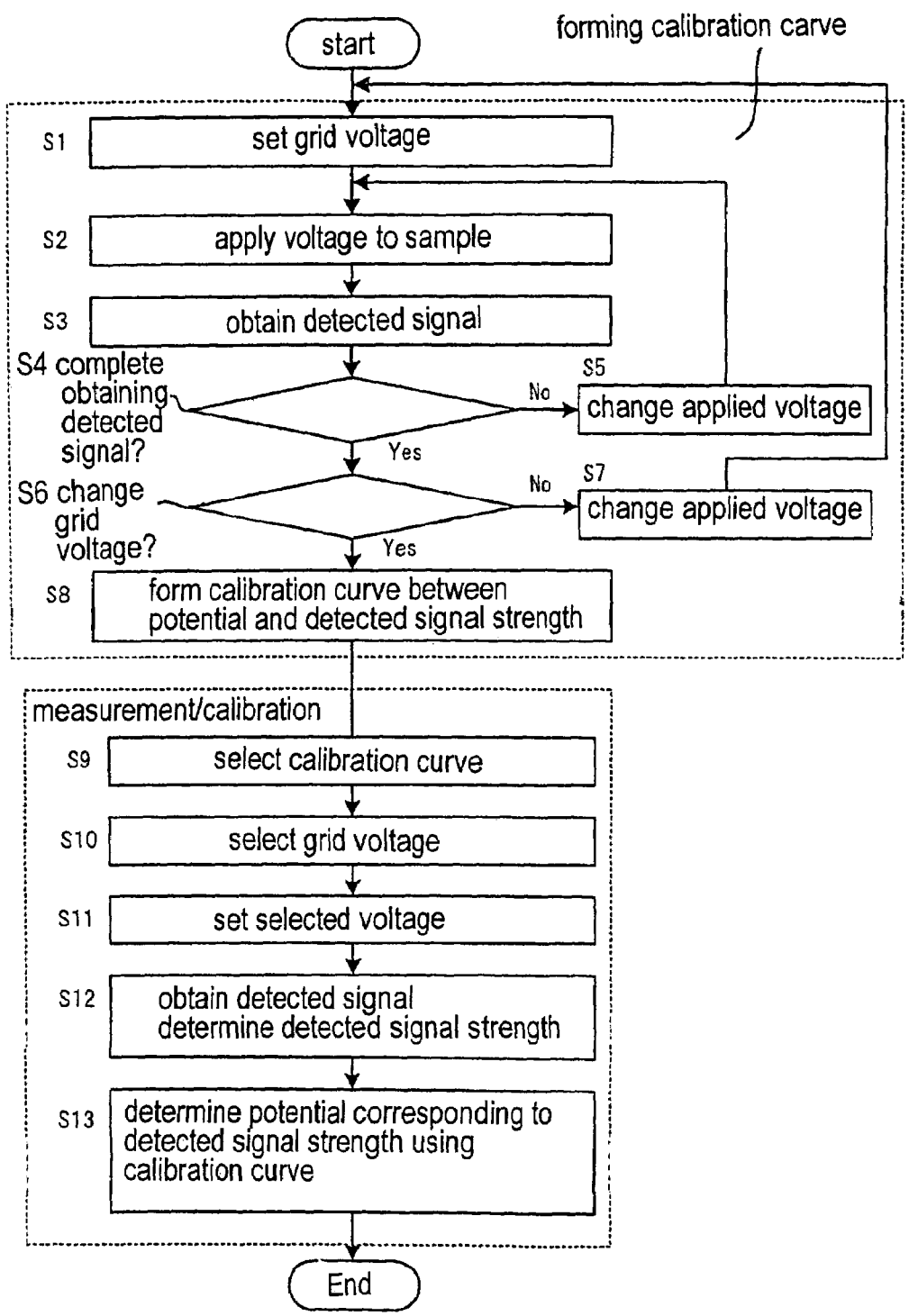
FIG. 3 is a flow chart, for explaining an operation of the TFT array inspection apparatus according to the embodiment of the invention.

An operation of the TFT array inspection apparatus of the invention will be explained next with reference to a flow-chart shown in FIG. 3 and schematic diagrams shown in FIGS. 4 and 5. As shown in FIG. 3, step S1 to step S8 are a process of forming the calibration curve; and step S9 to step S13 are a process of measuring the potential using the calibration curve.

Figure 4:
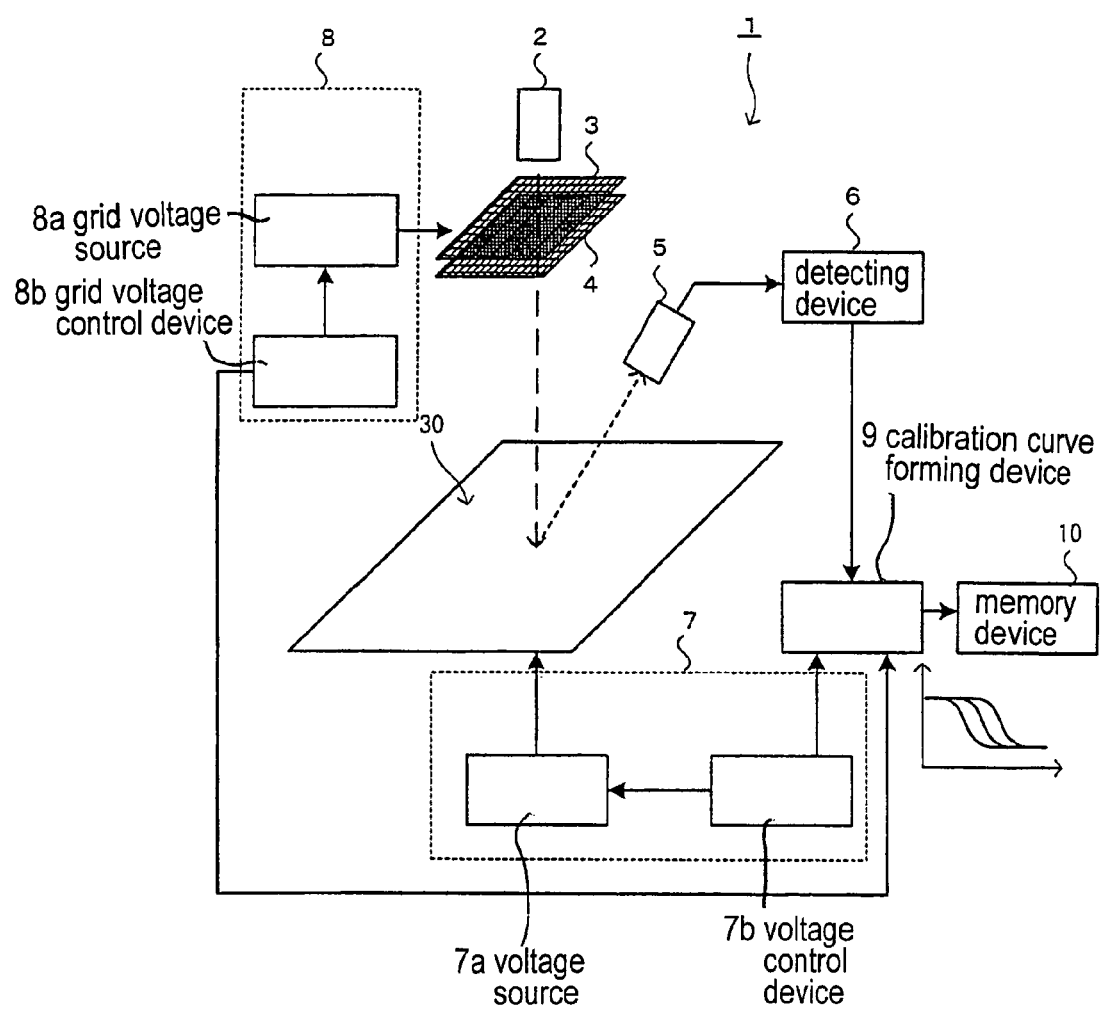
FIG. 4 is a schematic diagram for explaining an operation of the TFT array inspection apparatus according to the embodiment of the invention.

Referring to FIG. 4, in the process of forming the cali-bration curve, the grid potential setting device 8 sets specific potentials to the grids 3 and 4 (step S1). Then, the sample voltage changing device 7 applies a voltage to the sample 30 (step S2), and the detector 5 detects the signal (step S3). While the voltage applied to the sample 30 is changed, steps S2 and S3 are repeated (steps S4, S5). While the grid voltage is changed, the step S2 to step S5 are repeated (steps S6, S7).

In the process described above, the calibration curve forming device 9 receives information regarding the grid voltage set by the grid voltage setting device 8 and the voltage changed by the sample potential changing device 7, so that the characteristic of the detected signal strength and the sample potential is obtained with respect to the plural grid voltages. The characteristic showing a relationship between the detected signal strength and the sample poten-tial becomes the calibration curve for obtaining the sample potential from the detected signal strength. The calibration curve forming device 9 stores the calibration curve in the memory device 10 (step S8).

The steps S1 to S8 are performed in advance with respect to a sample having a characteristic same as that of the sample to be measured, and the result is used for the steps S9 to S13.

Referring to FIG. 5, a driving source 31 drives the sample 30 such as the TFT array. The base plate of the TFT array has a specific potential through the driving of the driving source 31. The TFT array inspection apparatus 1 determines the potential of the base plate driven by the driving source 31.

In the measuring/calibration process, the calibration device 11 selects a calibration curve from the memory device 10 suitable for a voltage range of the sample to be measured. For example, when the sample to be measured is the TFT array, a calibration curve suitable for calibrating the potential on the base plate of the TFT array is selected. That is, a calibration curve having a portion with good linearity is selected so that the potential on the base plate is in a voltage range of the portion (step S9).

The grid voltage corresponding to the selected calibration curve is selected (step S10), and the grid voltage selected by the grid voltage setting device 8 is set (step S11). The detecting device 6 obtains the detected signal under a state of the grid voltage to obtain the detected signal strength (step S12). The calibration device 11 determines a voltage corre-sponding to the detected signal strength using the calibration curve to thereby obtain a calibration output (step S13).

Figure 6B:
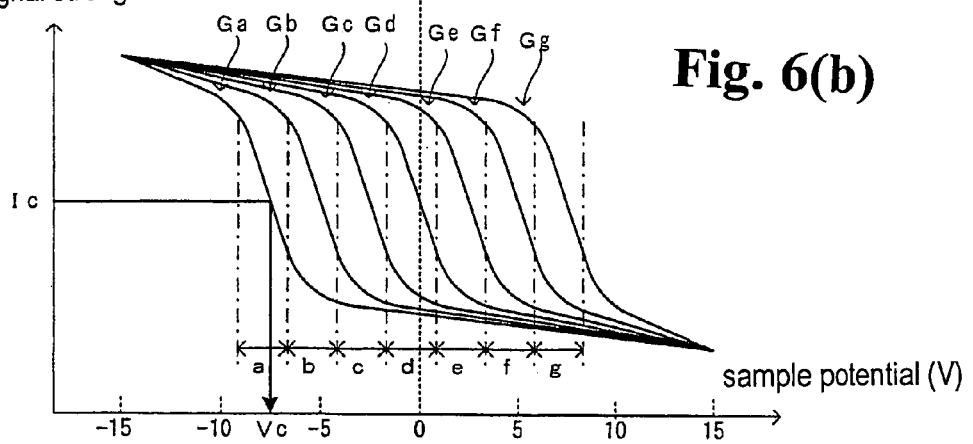
Figure 6C:
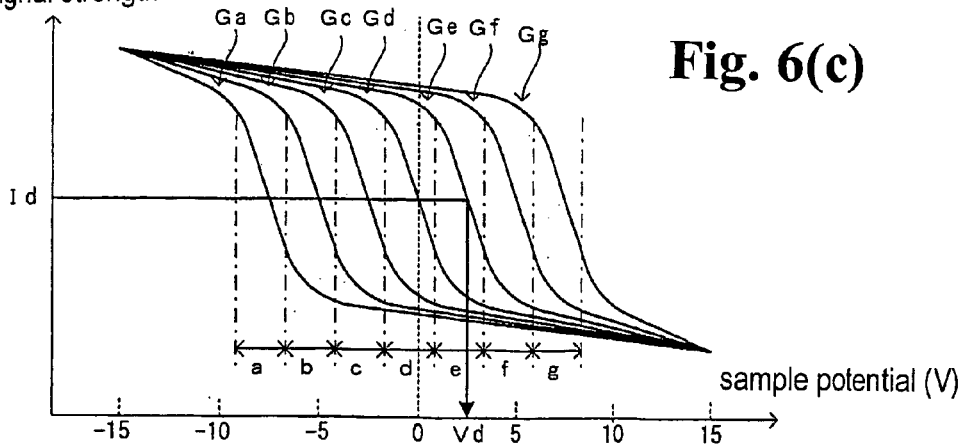
Figure 7:
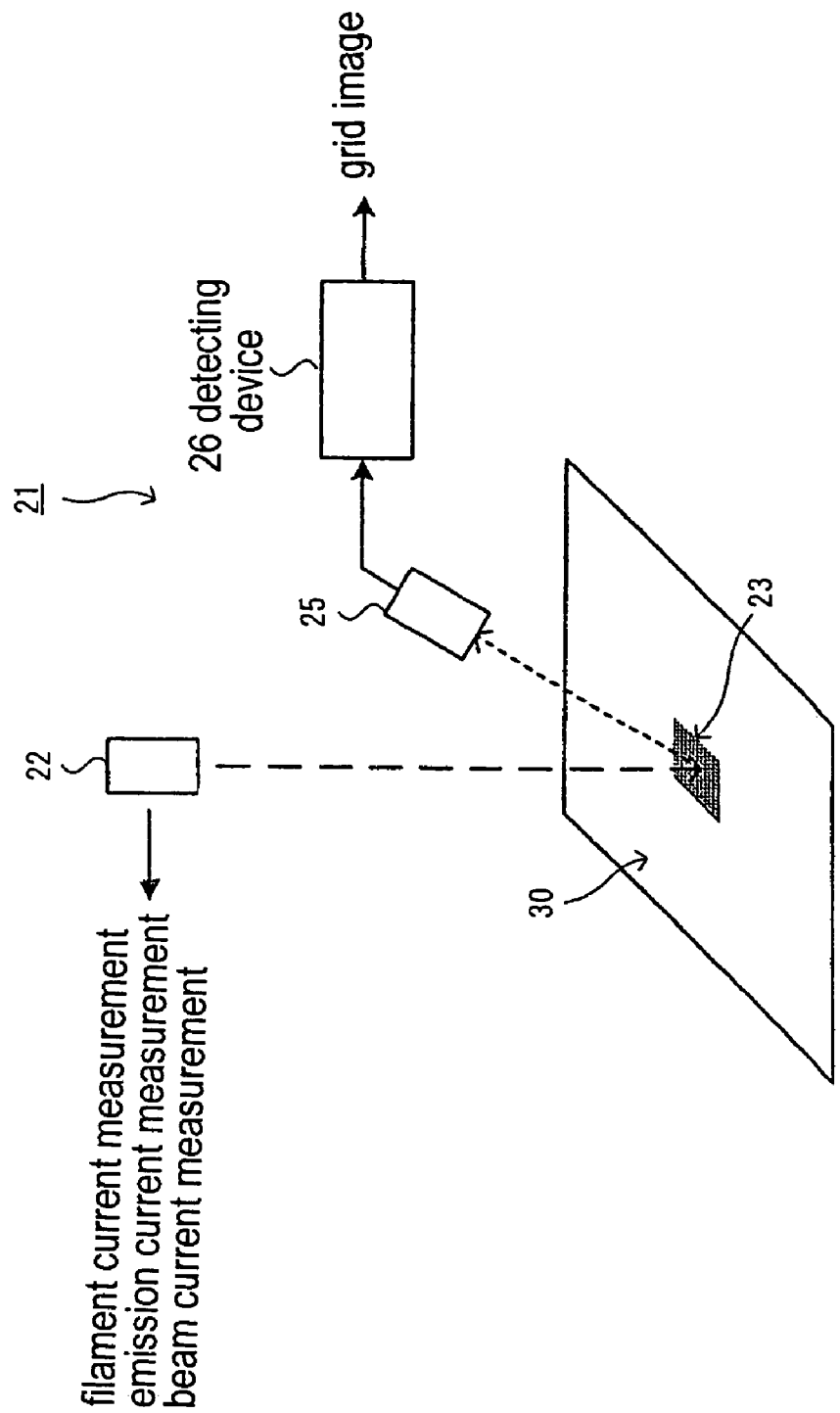
FIG. 7 is a schematic diagram for explaining calibration of a conventional electron gun.

FIGS. 6(b) and 6(c) show examples wherein the calibra-tion output is obtained by selecting from a plurality of calibration curves, respectively. Referring to FIG. 6(b), in a case that the voltage range of the sample is known in advance to be, for example, from −10 V to −5 V, a calibration curve having a portion with good linearity in the voltage region is selected. In the example, a calibration curve Ga having a portion with good linearity in a voltage region a is selected. A grid voltage corresponding to the selected cali-bration curve Ga is applied to the grid to obtain the detected signal strength. When the obtained detected signal strength is Ic, Vc can be obtained as the sample potential using the calibration curve Ga.

Referring to FIG. 6(c), in a case that the voltage range of the sample is known in advance to be, for example, from 0 V to +5 V, the calibration curve having a portion with good linearity in the voltage range is selected. In the example, a calibration curve Ge having a portion with good linearity in a voltage range e is selected. A grid voltage corresponding to the selected calibration curve Ge is applied to the grid to obtain the detected signal strength. When the obtained detected signal strength is Id, Vd can be obtained as the sample potential using the calibration curve Ge.

The present invention can be applied to not only the TFT array inspection apparatus but also an electron beam micro-analyzer; a scanning electron microscope; an X-ray diffrac-tometer; and a scanning beam device for forming a scanning image by two-dimensionally scanning a charge beam such as an electron beam and ion-beam on a sample.

The disclosure of Japanese Patent Application No. 2003-426759, filed on Dec. 24, 2003, is incorporated in the application.

While the invention has been explained with reference to the specific embodiments of the invention, the explanation is illustrative and the invention is limited only by the appended claims.

What is claimed is:

1. A TFT array inspection apparatus for inspecting a sample, comprising:
   an electron beam source for irradiating a first electron beam on the sample;
   a detecting device for detecting a second electron beam emitted from the sample by irradiation of the first electron beam to output a detected signal;
   a sample potential changing device for changing a sample potential; and
   a calibration device electrically connected to the detecting device and the sample potential changing device for calibrating the detected signal using a calibration curve to determine the sample potential, said calibration curve representing a relationship between a strength of the detected signal and the sample potential and show-ing the strength of the detected signal relative to a change of the sample potential.

2. A TFT array inspection apparatus according to claim 1, further comprising a calibration curve forming device elec-trically connected to the detecting device, the sample poten-tial changing device and the calibration device for forming the calibration curve, said calibration curve forming device receiving the sample potential from the sample potential changing device and the strength of the detected signal from the detecting device, and forming the calibration curve by the strength of the detected signal relative to the change of the sample potential inputted thereto.

3. A TFT array inspection apparatus according to claim 1, wherein said calibration device provides a plurality of calibration curves obtained under different conditions and calibrates the detected signal using one of the calibration curves.

4. A TFT array inspection apparatus according to claim 3, further comprising a calibration curve forming device electrically connected to the detecting device and the sample potential changing device, said calibration curve forming device receiving the sample potential from the sample potential changing device and the detected signal from the detecting device under the different conditions, and forming the calibration curves different in the different conditions by the strength of the detected signal relative to the change of the sample potential inputted thereto.

5. A TFT array inspection apparatus according to claim 4, further comprising a grid disposed at a downstream side of the electron beam source and a grid potential setting device for setting a potential of the grid so that the different conditions are set according to the potential of the grid.

6. A TFT array inspection apparatus according to claim 5, wherein said calibration curve forming device is connected to the grid potential setting device.

7. A TFT array inspection apparatus according to claim 6, further comprising a memory connected to the calibration curve forming device and the calibration device.

* * * * *